(12) United States Patent
Snutch

(10) Patent No.: US 6,310,059 B1
(45) Date of Patent: Oct. 30, 2001

(54) FUSED RING CALCIUM CHANNEL BLOCKERS

(75) Inventor: Terrance P. Snutch, Vancouver (CA)

(73) Assignee: NeuroMed Technologies, Inc., Vancouver (CA)

( * ) Notice: Subject to any disclaimer, the term of this patent is extended or adjusted under 35 U.S.C. 154(b) by 0 days.

(21) Appl. No.: 09/476,928

(22) Filed: Dec. 30, 1999

Related U.S. Application Data

(63) Continuation-in-part of application No. 09/401,699, filed on Sep. 23, 1999, which is a continuation-in-part of application No. 09/107,037, filed on Jun. 30, 1998, now Pat. No. 6,011,035
(60) Provisional application No. 60/172,765, filed on Dec. 20, 1999.

(51) Int. Cl.[7] .......................... A61K 31/54; A61K 31/50; A61K 31/435
(52) U.S. Cl. .................. 514/222.2; 514/228; 514/247; 514/277
(58) Field of Search ............... 514/222.2, 228, 514/247, 277

(56) References Cited

U.S. PATENT DOCUMENTS

| | | |
|---|---|---|
| 3,288,795 | 11/1966 | Irikura et al. . |
| 4,188,485 | 2/1980 | Kukla . |
| 4,918,073 | 4/1990 | Ruger et al. . |
| 5,386,025 | 1/1995 | Jay et al. ........................ 536/23.5 |
| 5,428,038 | 6/1995 | Chatterjee et al. .................. 514/253 |
| 5,623,051 | 4/1997 | Catterall et al. ..................... 530/324 |
| 5,646,149 | 7/1997 | Hellberg et al. ..................... 514/253 |
| 5,703,071 | 12/1997 | Itoh et al. ........................ 514/218 |

FOREIGN PATENT DOCUMENTS

| | | |
|---|---|---|
| 17 70 218 | 10/1974 | (DE) . |
| 0 187 524 | 7/1986 | (EP) . |
| 0 458387 | 11/1991 | (EP) . |
| 504 202 | 1/1983 | (ES) . |
| 514 167 | 4/1983 | (ES) . |
| 1 522 688 | 4/1968 | (FR) . |
| 1 425 710 | 2/1976 | (GB) . |
| 1 513 883 | 6/1978 | (GB) . |
| WO 99/15129 | 4/1999 | (WO) . |
| WO 99/25686 | 5/1999 | (WO) . |

OTHER PUBLICATIONS

Bourinet et al., "Splicing of $\alpha_{1A}$ Subunit Gene Generates Phenotypic Variants of P– and Q–Type Calcium Channels," Nature Neuroscience (1999) 2:407–415.

Cribbs et al., "Cloning and Characterization of $\alpha$1H from Human Heart, A Member of the T–Type $Ca^{2+}$ Channel Gene Family," Circulation Research (1998) 83:103–109.

De Waard et al., "Structural and Functional Diversity of Voltage–Activated Calcium Ion Channels," Channels (Narahashi, T. ed. Plenum Press, NY 1997) 4:41–87.

Dooley, "Lomerizine Kanebo KK" Current Opinion in CPNS Investigational Drugs (1999) 1(1):116–125.

Dunlap et al., "Exocytotic $Ca^{2+}$ Channels in Mammalian Central Neurons," Trends Neurosci (1995) 18:89–98.

Galizzi et al., "Neuroleptics of the Diphenylbutylpiperidine Series are Potent Calcium Channel Inhibitors," Proc Natl Acad Sci USA (1986) 83:7513–7517.

Gould et al., "Antischizophrenic Drugs of the Diphenylbutylpiperidine Type Act as Calcium Channel Antagonists," Proc Natl Acad Sci (1983) 80:5122–5125.

(List continued on next page.)

Primary Examiner—Raymond Henley, III
(74) Attorney, Agent, or Firm—Morrison & Foerster LLP

(57) ABSTRACT

Compounds of the formula

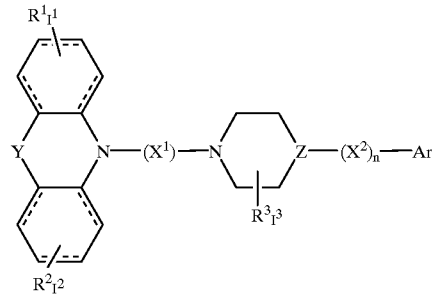

or salts thereof, wherein the variable are as defined herein are useful as calcium channel blockers.

27 Claims, No Drawings

OTHER PUBLICATIONS

Grantham et al., "Fluspirilene Block of N–Type Calcium Current in NGF–Differentiated PC12 Cells," Brit J Pharmacol (1994) 111:438–488.

Ito et al., "U–92032, a T–Type $Ca^{2+}$ Channel Blocker and Antioxidant, Reduces Neuronal Ischemic Injuries," Eur J Pharmacol (1994) 257:203–210.

King et al., "Substituted Diphenylbutylpiperidines Bind to a Unique High Affinity Site on the L–Type Calcium Channel," J Biol Chem (1989) 264:5633–5641.

Lee et al., "Cloning and Expression of a Novel Member of the Low Voltage–Activated T–Type Calcium Channel Family," Journal of Neuroscience (1999) 19:1912–1921.

McCleskey et al., "Functional Properties of Voltage Dependent Calcium Channels," Curr Topics Membr (1991) 39:295–326.

Perez–Reyes et al., "Molecular Characterization of a Neuronal Low–Voltage–Activated T–Type Calcium Channel," Nature (1998) 391:896–900.

Sather et al., "Distinctive Biophysical and Pharmacological Properties of Class A (BI) Calcium Channel $\alpha_1$ Subunits," Neuron (1993) 11:291–303.

Stea et al., "Localization and Functional Properties of a Rat Brain $\alpha_{1A}$ Calcium Channel Reflect Similarities to Neuronal Q–and P–Type Channels," Proc Natl Acad Sci USA (1994) 91:10576–10580.

Stea et al., Handbook of Receptors and Channels (North, R.A. ed. CRC Press 1995) 113–151.

Cohan, S. et al. (1991). *Annals of the New York Academy of Sciences* 635:397–399.

Database WPI Week 9711 Derwent Publications Ltd., London, GB; Abstract JP 09 003067, XP002133055 (Hisamitsu Pharm Co Ltd.) Jan. 7, 1997.

Dhainaut et al. (1992). *J. of Medicinal Chemistry* 35:2481–2496.

Estep, K. et al. (1995). *J. of Medicinal Chemistry* 38(14):2582–2595.

Glamkowski, E. et al. (1977). *J of Medicinal Chemistry* 20(11):1485–1489.

Lehmann et al. (1988). *Archiv der Pharmazie* 321(11):807–812.

Miyano, S. et al. (1990). *Chem Pharm Bull* 38(6):1570–1574.

Ohtaka, H. et al. (1987). *Chem Pharm Bull* 35(8):3270–3275.

Ohtaka, H. et al. (1987). *Chem Pharm Bull* 35(10):4117–4123.

Prasad, R. et al. (1968). *J of Medicinal Chemistry* 11(6):1144–1150.

Tytgat, J. et al. (1991). *Brain Research* 549(1):112–117.

Uneyama, H. et al. (1998). *Calcium Ion Modulators*, Sel Pap Satell Symp 13–23.

Vadodaria, D. et al. (1969). *J of Medicinal Chemistry* 12:860–865.

Zikolova, S. et al. (1972). *Tr. Nauchnoizsled Khim–Farm Inst* 8:59–67.

Zikolova, S. et al. (1984). *Tr. Nauchnoizsled Khim–Farm Inst* 14:23–28.

Archibald, J. and Benke, G. (1974). *J. Med Chem* 17(7):736–739.

Boissier, J.–R. et al. (1967). *Therapie* 22(2):375–382.

Golinski, M. et al. (1995). *Bioconjugate Chem* 6(5):549–557.

Nakanishi, M. et al. (1970). *J Med Chem* 13(4):644–648.

Toldy, L. et al. (1965). *Acta Chim Acad Sci Hung* 44:301–325.

Tsutsui, I. et al. (1987). *J Membr Biol* 96(1):65–73.

Tsutsui, I. et al. (1987). *J Membr Biol* 96(1):75–84.

FUSED RING CALCIUM CHANNEL BLOCKERS

This application is a C-I-P of Ser. No. 09/401,699 filed Sep. 23,1999, which is a C-I-P of Ser. No. 09/107,037 filed Jun. 30, 1998 U.S. Pat. No. 6,011,035, which claims benefit of Ser. No. 60/172,765 filed Dec. 20, 1999.

TECHNICAL FIELD

The invention relates to compounds useful in treating conditions associated with calcium channel function. More specifically, the invention concerns compounds containing a fused ring system and 6-membered heterocyclic moieties that are useful in treatment of conditions such as stroke and pain.

BACKGROUND ART

Native calcium channels have been classified by their electrophysiological and pharmacological properties as T, L, N, P and Q types (for reviews see McCleskey, E. W. et al. *Curr Topics Membr* (1991) 39:295–326, and Dunlap, K. et al. *Trends Neurosci* (1995) 18:89–98). T-type (or low voltage-activated) channels describe a broad class of molecules that transiently activate at negative potentials and are highly sensitive to changes in resting potential. The L, N, P and Q-type channels activate at more positive potentials (high voltage activated) and display diverse kinetics and voltage-dependent properties. There is some overlap in biophysical properties of the high voltage-activated channels, consequently pharmacological profiles are useful to further distinguish them. L-type channels are sensitive to dihydropyridine agonists and antagonists, N-type channels are blocked by the *Conus geographus* peptide toxin, ω-conotoxin GVIA, and P-type channels are blocked by the peptide ω-agatoxin IVA from the venom of the funnel web spider, *Agelenopsis aperta*. A fourth type of high voltage-activated calcium channel (Q-type) has been described, although whether the Q- and P-type channels are distinct molecular entities is controversial (Sather, W. A. et al. *Neuron* (1995) 11:291–303; Stea, A. et al. *Proc Natl Acad Sci USA* (1994) 91:10576–10580; Bourinet, E. et al. *Nature Neuroscience* (1999) 2:407–415). Several types of calcium conductances do not fall neatly into any of the above categories and there is variability of properties even within a category suggesting that additional calcium channels subtypes remain to be classified.

Biochemical analyses show that neuronal high voltage activated calcium channels are heterooligomeric complexes consisting of three distinct subunits ($\alpha_1$, $\alpha_2\delta$ and $\beta$)(reviewed by De Waard, M. et al. *Ion Channels* (1997) vol. 4, Narahashi, T. ed. Plenum Press, NY). The a., subunit is the major pore-forming subunit and contains the voltage sensor and binding, sites for calcium channel antagonists. The mainly extracellular $\alpha_2$ is disulfide-linked to the transmembrane $\delta$ subunit and both are derived from the same gene and are proteolytically cleaved in vivo. The $\beta$ subunit is a nonglycosylated, hydrophilic protein with a high affinity of binding to a cytoplasmic region of the $\alpha_1$ subunit. A fourth subunit, $\gamma$, is unique to L-type calcium channels expressed in skeletal muscle T-tubules. The isolation and characterization of γ-subunit-encoding cDNAs is described in U.S. Pat. No. 5,386,025 which is incorporated herein by reference.

Recently, each of these $\alpha_1$ subtypes has been cloned and expressed, thus permitting more extensive pharmacological studies. These channels have been designated $\alpha_{1A}$–$\alpha_{1I}$ and $\alpha_{1S}$ and correlated with the subtypes set forth above. $\alpha_{1A}$ channels are of the P/Q type; $\alpha_{1B}$ represents N; $\alpha_{1C}$, $\alpha'_{1D}$, $\alpha_{1F}$ and $\alpha_{1S}$ represent L; $\alpha_{1E}$ represents a novel type of calcium conductance, and $\alpha_{1G}$–$\alpha_{1I}$ represent members of the T-type family, reviewed in Stea, A. et al. in Handbook of Receptors and Channels (1994), North, R. A. ed. CRC Press; Perez-Reyes, et al. *Nature* (1998) 391:896–900; Cribbs, L. L. et al. *Circulation Research* (1998) 83:103–109; Lee, J. H. et al. *Journal of Neuroscience* (1999) 19:1912–1921.

Further details concerning the function of N-type channels, which are presynaptic channels, have been disclosed, for example, in U.S. Pat. No. 5,623,051, the disclosure of which is incorporated herein by reference. As described, N-type channels possess a site for binding, syntaxin, a protein anchored in the presynaptic membrane. Blocking this interaction also blocks the presynaptic response to calcium influx. Thus, compounds that block the interaction between syntaxin and this binding site would be useful in neural protection and analgesia. Such compounds have the added advantage of enhanced specificity for presynaptic calcium channel effects.

U.S. Pat. No. 5,646,149 describes calcium channel antagonists of the formula A—Y—B wherein B contains a piperazine or piperidine ring directly linked to Y. An essential component of these molecules is represented by A, which must be an antioxidant; the piperazine or piperidine itself is said to be important. The exemplified compounds contain a benzhydril substituent, based on known calcium channel blockers (see below). U.S. Pat. No. 5,703,071 discloses compounds said to be useful in treating ischemic diseases. A mandatory portion of the molecule is a tropolone residue; among the substituents permitted are piperazine derivatives, including their benzhydril derivatives. U.S. Pat. No. 5,428,038 discloses compounds which are said to exert a neural protective and antiallergic effect. These compounds are coumarin derivatives which may include derivatives of piperazine and other six-membered heterocycles. A permitted substituent on the heterocycle is diphenylhydroxymethyl. Thus, approaches in the art for various indications which may involve calcium channel blocking activity have employed compounds which incidentally contain piperidine or piperazine moieties substituted with benzhydril but mandate additional substituents to maintain functionality.

Certain compounds containing both benzhydril moieties and piperidine or piperazine are known to be calcium channel antagonists and neuroleptic drugs. For example, Gould, R. J. et al. *Proc Natl Acad Sci USA* (1983) 80:5122–5125 describes antischizophrenic neuroleptic drugs such as lidoflazine, fluspirilene, pimozide, clopimozide, and penfluridol. It has also been shown that fluspirilene binds to sites on L-type calcium channels (King, V. K. et al. *J Biol Chem* (1989) 264:5633–5641) as well as blocking N-type calcium current (Grantham, C. J. et al. *Brit J Pharmacol* (1944) 111:483–488). In addition, Lomerizine, developed by Kanebo K K, is a known non-specific calcium channel blocker. A review of publications concerning Lomerizine is found in Dooley, D., *Current Opinion in CPNS Inivestigational Drugs* (1999) 1:116–125.

The present invention is based on the recognition that compounds comprising a six-membered heterocyclic ring containing at least one nitrogen coupled to a constrained fused ring moiety and to a hydrophobic cluster (each optionally through a linker) provide calcium channel blocking activity. These compounds are useful, for example, for treating stroke and pain. By focusing on these moieties, compounds useful in treating indications associated with unwanted calcium channel activity and combinatorial libraries that contain these compounds can be prepared.

DISCLOSURE OF THE INVENTION

The invention relates to compounds useful in treating conditions such as stroke, head trauma, migraine, chronic, neuropathic and acute pain, epilepsy, hypertension, cardiac arrhythmias, and other indications associated with calcium metabolism, including synaptic calcium channel-mediated functions. The compounds of the invention are constrained fused ring derivatives of piperidine or piperazine linked to hydrophobic substituents which enhance the calcium channel blocking activity. Thus, in one aspect, the invention is directed to therapeutic methods that employ compounds of the formulas

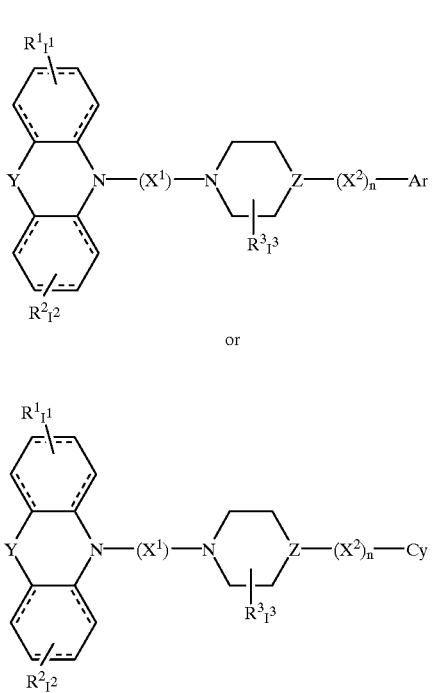

wherein Z is N or CH;
wherein n is 0 or 1;
$X^1$ and $X^2$ are linkers;
Ar represents one or two substituted or unsubstituted aromatic or heteroaromatic rings, and
Cy represents one or two substituted or unsubstituted aliphatic cyclic or heterocyclic moieties, or consists of one substituted or unsubstituted aliphatic cyclic or heterocyclic moiety and one substituted or unsubstituted aromatic or heteroaromatic moiety,
Y is O, S, NR or $CR_2$ where R is H or alkyl (1–6C);
each $l^1$ and $l^2$ is independently 0–4;
$l^3$ is 0 or 1;
each of $R^1$, $R^2$ and $R^3$ is independently alkyl (1–6C), aryl (6–10C) or arylalkyl (7–16C) optionally containing 1–4 heteroatoms selected from the group consisting of halo, N, P, O, and S or may independently be halo, OR, SR, $NR_2$, OOCR, NROCR, COR, COOR, $CONR_2$, $CF_3$, CN or $NO_2$, wherein R is H or alkyl (1–6C), and wherein the dotted lines represent optional π-bonds, or compounds of formulas (1a) or (1b) where $(X^2)_n$Ar or $(X^2)_n$Cy is replaced by substituted or unsubstituted alkyl (1–6C).

The invention is directed to methods to antagonize calcium channel activity using the compounds of formulas (1a) or (1b) and thus to treat associated conditions. It will be noted that the conditions may be associated with abnormal calcium channel activity, or the subject may have normal calcium channel function which nevertheless results in an undesirable physical or metabolic state that can be benefited by lowering calcium transport. In another aspect, the invention is directed to pharmaceutical compositions containing these compounds.

The invention is also directed to combinatorial libraries containing the compounds of formulas (1a) or (1b) and to methods to screen these libraries for members containing particularly potent calcium channel blocking activity including channel blocking activity of particular types or for members that antagonize other ion channels.

MODES OF CARRYING OUT THE INVENTION

The compounds of formulas (1a) or (1b), useful in the methods of the invention, exert their desirable effects through their ability to antagonize the activity of calcium channels, including those which are synaptic in their activity. While the compounds of formulas (1a) or (1b) generally have this activity, the availability of a multiplicity of calcium channel blockers permits a nuanced selection of compounds for particular disorders. Thus, the availability of this class of compounds provides not only a genus of general utility in indications that are affected by excessive calcium channel activity, but also provides a large number of compounds which can be mined and manipulated for specific interaction with particular forms of calcium or other channels. The availability of recombinantly produced calcium channels of the $\alpha_{1A}$–$\alpha_{1I}$ and $\alpha_{1S}$ types set forth above, facilitates this selection process. Dubel, S. J. et al. *Proc Natl Acad Sci USA* (1992) 89:5058–5062; Fujita, Y. et al. *Neuron* (1993) 10:585–598; Mikami, A. et al. *Nature* (1989) 340:230–233; Mori, Y. et al. *Nature* (1991) 350:398–402; Snutch, T. P. et al. *Neuron* (1991) 7:45–57; Soong, T. W. et al. *Science* (1993) 260:1133–1136; Tomlinson, W. J. et al. *Neuropharmacolooy* (1993) 32:1117–1126; Williams, M. E. et al. *Neuron* (1992) 8:71–84; Williams, M. E. et al. *Science* (1992) 257:389–395; Perez-Reyes, et al. *Nature* (1998) 391:896–900; Cribbs, L. L. et al. *Circulation Research* (1998) 83:103–109; Lee, J. H. et al. *Journal of Neuroscience* (1999) 19:1912–1921.

Thus, while it is known that calcium channel activity is involved in a multiplicity of disorders, the types of channels associated with particular conditions is the subject of ongoing data collection. The association of N-type channels in conditions associated with neural transmission would indicate that compounds which target N-type receptors are useful in these conditions. Many of the members of the genus of compounds of formulas (1a) or (1b) target N-type channels; other members of the genus target other channels, and some members target several channels.

Among the conditions associated in which blocking calcium transport would be of therapeutic value are stroke, head trauma, mood disorders, schizophrenia, and chronic, neuropathic and acute pain. Calcium transport, including that associated with N-type channels, is also implicated in other neurological disorders such as migraine, epilepsy and certain degenerative disorders. Other conditions that may be treated include anxiety, depression and other psychoses. Cardiovascular conditions affected by calcium flux include hypertension and cardiac arrhythmias.

The availability of the libraries containing the compounds of formulas (1a) or (1b) also provides a source of compounds which may be screened for activity with regard to calcium channels and other ion channels. Other ion channels are also associated with conditions that are susceptible to treatment. Blockers of sodium channels, for example, are useful as local anesthetics, and in treating cardiac arrhythmias, as anticonvulsants, and in treating hyperkalemic periodic paralysis. Potassium channel blockers are useful in treating hypertension and cardiac arrhythmias; various other receptors are associated with psychoses, schizophrenia, depression, and apnea. Thus, the library of compounds of the invention is useful in standard screening techniques as a source of effective pharmaceutical compounds.

Synthesis

The compounds of the invention may be synthesized using conventional methods. Illustrative of such methods are the following schemes.

Scheme 1
(Phenanthrothiazine Derivatives)

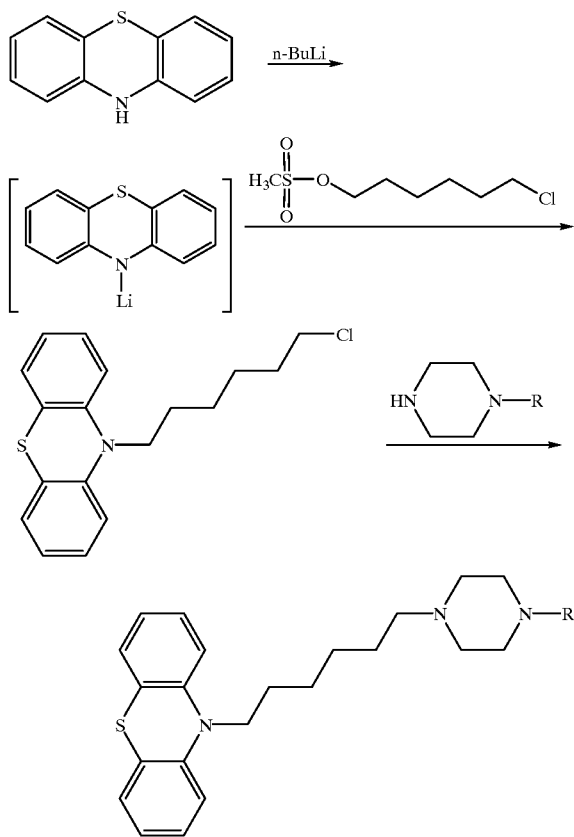

As shown in Scheme 1, phenanthrothiazine or the corresponding compound wherein S is replaced by O, NR or $CR_2$, is reacted with butyllithium and then treated with the desired mesylate to generate the intermediate wherein the linker $X^1$ is coupled to the nitrogen of the phenanthrothiazine. In the instance wherein Y is NR, especially NH, and where the phenylene rings are substituted, mixtures of isomers may result, which may then be separated as desired. The resulting coupled compound is then reacted with the desired piperazine or piperidine to generate the compounds of the invention. The mesylate required for step 1 can readily be generated by treating the corresponding omega-hydroxybromide with methylsulfonyl chloride. For compounds wherein Z is CH, the appropriate substituted piperidine can be prepared by treating the corresponding pyridone with the appropriate amine and reducing with a mild reducing agent, as shown in Scheme 2.

Scheme 2

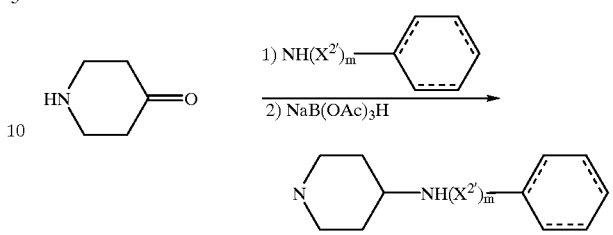

Preferred Embodiments

The compounds of formulas (1a) or (1b) are defined as shown in terms of the embodiments of their various substituents:

Y may be O, S, NR or $CR_2$; preferably each R is H. More preferably, Y is S.

Z may be N or CH.

Preferably, each of $R^1$ and $R^2$ is independently alkyl (1–6C), arylalkyl (7–16C), halo, OR, SR, $NR_2$, OOCR, NROCR, COR, COOR or $CONR_2$ wherein each R is independently H or alkyl (1–6C) or may be CN, $CF_3$ or $NO_2$ (the "substituents"). Preferred embodiments of $l^1$ and $l^2$ include those 1) where one substituent is ortho or meta to Y and 2) where two substituents are in the positions meta and para to Y. Especially preferred forms of $R^1$ and $R^2$ include phenyl, phenylalkyl, F, Cl, Br, I, $CF_3$, OR, NR2 and alkyl. Particularly preferred are F, OMe, $NH_2$, $NMe_2$, NHOAc, $CONH_2$, Br, COOEt, and COOMe.

$R^3$ may be alkyl (1–6C) aryl (6–10C) or arylalkyl (7–16C) optionally containing 1–4 heteroatoms selected from the group consisting of N, P, O, S, and halo; preferred embodiments of $R^3$ include methyl. $R^3$ may also include halo, OR, SR, $NR_2$, OOCR, NROCR, COR, COOR or $CONR_2$ wherein each R is independently H or alkyl (1–6C) or may be CN, $CF_3$ or $NO_2$. Typically, $l^3$ is 0 or 1, preferably 0.

As n may be 0 or 1, $X^2$ may be present or not. $X^1$ and $X^2$ are suitable linkers containing 1–10C which may be saturated or unsaturated and may contain a ring. The linker may also contain one or two heteroatoms selected from N, O and S and may be substituted with the "substituents" listed above. Preferred embodiments of $X^1$ and $X^2$ include —$(CH_2)_a$— wherein a is 1–10, preferably 1–6, —$(CH_2)_b$CO— or —$CO(CH_2)_b$, where b is 1–9, and —$(CH_2)_c$CH=CH, where c is 0–4. Also preferred particularly for $X^2$ is —$NH(CH_2)_d$— or —$NHCO(CH_2)_d$—where d is 1–8, when Z is CH.

Thus, formulas (1a) and (1b) are similar, except that compounds of formula (1a) contain aromatic substituents linked to the heterocyclic 6-membered ring and those of (1b) contain aliphatic cyclic or heterocyclic moieties. In each case, preferably when $X^2$ is present, $X^2$ represents a linker which spaces the Ar or Cy moiety from Z at a distance of 3–20 Å, and may contain at least one heteroatom which is nitrogen or oxygen. Included in such linkers are amines and carbonyl functionalities, including amides. The linker may also be unsaturated or may be an alkylene group. Typically, $X^2$ is $(CH_2)_{1-10}$ or —$CO(CH_2)_{1-9}$— or $(CH_2)_{1-5}$—CH=CH—$(CH_2)_{0-3}$—. Similarly, $X^1$ spaces the constrained fused ring system from the nitrogen of the heterocyclic ring at a distance of 3–20 Å.

For $X^2$, when there are two aromatic or heterocyclic or other cyclic moieties, $X^2$ must accommodate this and a typical embodiment is —$(CH_2)_{0-9}$—CH. $X^2$ may also contain a π-bond, e.g., —$(CH_2)_{0-5}$CH=C, for such accommodation.

In preferred forms of formulas (1a) and (1b), $X^1$ is $(CH_2)_{1-5}CO(CH_2)_{0-3}$ or $(CH_2)_{1-5}NH(CH_2)_{1-3}$ or $(CH_2)_{1-5}CONH(CH_2)_{1-3}$.

Preferred embodiments for $X^2$ are similar except that in instances where Ar or Cy represent two rings, the two rings are coupled to CH or to a π-bonded carbon as the terminal portion of the linker $X^2$.

Although it is preferred that $l^1$ and $l^2$ are both 0, substitution by $R^1$ and $R^2$ in the constrained fused ring system is permitted as set forth in the description of the invention above.

It is believed that halogenation of the compounds of the invention is helpful in modulating the in vivo half-life, and it may be advantageous to include halogen substituents as $R^1$ and $R^2$. In formulas (1a) and (1b), such substituents may also be included on Ar and Cy.

The invention compounds may also be supplied as pharmaceutically acceptable salts. Pharmaceutically acceptable salts include the acid addition salts which can be formed from inorganic acids such as hydrochloric, sulfuric, and phosphoric acid or from organic acids such as acetic, propionic, glutamic, glutaric, as well as acid ion-exchange resins.

Utility and Administration

For use as treatment of human and animal subjects, the compounds of the invention can be formulated as pharmaceutical or veterinary compositions. Depending on the subject to be treated, the mode of administration, and the type of treatment desired e.g., prevention, prophylaxis, therapy; the compounds are formulated in ways consonant with these parameters. A summary of such techniques is found in Remington's *Pharmaceutical Sciences*, latest edition, Mack Publishing Co., Easton, Pa., incorporated herein by reference.

In general, for use in treatment, the compounds of formulas (1a) and (1b) may be used alone, as mixtures of two or more compounds of formulas (1a) and (1b) or in combination with other pharmaceuticals. Depending on the mode of administration, the compounds will be formulated into suitable compositions to permit facile delivery.

Formulations may be prepared in a manner suitable for systemic administration or topical or local administration. Systemic formulations include those designed for injection (e.g., intramuscular, intravenous or subcutaneous injection) or may be prepared for transdermal, transmucosal, or oral administration. The formulation will generally include a diluent as well as, in some cases, adjuvants, buffers, preservatives and the like. The compounds can be administered also in liposomal compositions or as microemulsions.

For injection, formulations can be prepared in conventional forms as liquid solutions or suspensions or as solid forms suitable for solution or suspension in liquid prior to injection or as emulsions. Suitable excipients include, for example, water, saline, dextrose, glycerol and the like. Such compositions may also contain amounts of nontoxic auxiliary substances such as wetting or emulsifying agents, pH buffering agents and the like, such as, for example, sodium acetate, sorbitan monolaurate, and so forth.

Various sustained release systems for drugs have also been devised. See, for example, U.S. Pat. No. 5,624,677.

Systemic administration may also include relatively noninvasive methods such as the use of suppositories, transdermal patches, transmucosal delivery and intranasal administration. Oral administration is also suitable for compounds of the invention. Suitable forms include syrups, capsules, tablets, as in understood in the art.

For administration to animal or human subjects, the dosage of the compounds of the invention is typically 0.1–15 mg/kg, preferably 0.1–1 mg/kg. However, dosage levels are highly dependent on the nature of the condition, the condition of the patient, the judgment of the practitioner, and the frequency and mode of administration.

Screening Methods

The compounds of the invention can be synthesized individually using methods known in the art per se, or as members of a combinatorial library. In general, the constrained fused ring portion of the molecule, typically containing any $R^1$ and $R^2$ substituents is coupled, along with any linking moiety, to the nitrogen of the piperazine or piperidine ring. This ring itself is generally appropriately substituted with $(X^2)_n$—Ar or $(X^2)_n$—Cy prior to this coupling. Typically, the constrained fused ring-linker portion is supplied containing a suitable electron-withdrawing leaving group, thus effecting the coupling to the ring nitrogen.

In addition to condensing a halogenated derivative of a constrained fused ring moiety to the nitrogen-containing heterocycle, additional conventional ways of condensing the relevant portions of the molecule can be used. For example, a brominated form of appropriately substituted constrained fused ring (containing at least an ethyl group at the ring nitrogen) may be converted to a Grignard reagent which can then be condensed with, for example, the piperidine, or piperazine ring extended at the nitrogen through the moiety $(CH_2)_n$CHO wherein n is an integer from 1–4.

Synthesis of combinatorial libraries is now commonplace in the art. Suitable descriptions of such syntheses are found, for example, in Wentworth, Jr., P. et al. *Current Opinion in Biol* (1993) 9:109–115; Salemme, F. R. et al *Structure* (1997) 5:319–324. The libraries contain compounds with various embodiments of $R^1$, $R^2$, $R^3$, $X^1$, $X^2$, Y and Z. These libraries, which contain, as few as 10, but typically several hundred members to several thousand members, may then be screened for compounds which are particularly effective against a specific subtype of calcium channel. In addition, using standard screening protocols, the libraries may be screened for compounds which block additional channels such as sodium channels, potassium channels and the like.

Methods of performing these screening functions are well known in the art. Typically, the channel to be targeted is expressed at the surface of a recombinant host cell such as human embryonic kidney cells. The ability of the members of the library to bind the channel is measured, for example, by the ability of the compound in the library to displace a labeled binding ligand such as the ligand normally associated with the channel or an antibody to the channel. More typically, ability to antagonize the channel is measured in the presence of the appropriate agonist and the ability of the compound to interfere with the signal generated is measured using standard techniques.

In more detail, one method involves the binding of radiolabeled agents that interact with, e.g., the calcium channel and subsequent analysis of equilibrium binding measurements including, but not limited to, on rates, off rates, $K_d$ values and competitive binding by other molecules. Another method involves the screening for the effects of compounds by electrophysiological assay whereby individual cells are impaled with a microelectrode and currents through the channel are recorded before and after application of the compound of interest. Another method, high-throughput spectrophotometric assay, utilizes loading of the cell lines with a fluorescent dye sensitive to intracellular calcium concentration and subsequent examination of the effects of compounds on the ability of depolarization by potassium chloride or other means to alter intracellular calcium levels.

The following examples are intended to illustrate but not to limit the invention.

EXAMPLE 1

Assay of N-type Calcium Channel Blocking Activity

Antagonist activity was measured using whole cell patch recordings on human embryonic kidney cells either stably or transiently expressing rat $\alpha_{1B}+\alpha_{2b}+\beta_{1b}$ channels with 5 mM barium as a charge carrier.

For transient expression, host cells, such as human embryonic kidney cells, HEK 293 (ATCC#CRL 1573) are grown in standard DMEM medium supplemented with 2 mM glutamine and 10% fetal bovine serum. HEK 293 cells are transfected by a standard calcium-phosphate-DNA coprecipitation method using the rat $\alpha_{1B}+\beta_{1b}+\alpha_2\delta$ N-type calcium channel subunits in a vertebrate expression vector (for example, see Current Protocols in Molecular Biology).

After an incubation period of from 24 to 72 hrs the culture medium was removed and replaced with external recording solution (see below). Whole cell patch clamp experiments were performed using an Axopatch 200B amplifier (Axon Instruments, Burlingame, Calif.) linked to an IBM compatible personal computer equipped with pCLAMP software. Borosilicate glass patch pipettes (Sutter Instrument Co., Novato, Calif.) were polished (Microforge, Narishige, Japan) to a resistance of about 4 MΩ when filled with cesium methanesulfonate internal solution (composition in MM: 109 $CsCH_3SO_4$, 4 $MgCl_2$, 9 EGTA, 9 HEPES, pH 7.2). Cells were bathed in 5 mM $Ba^{++}$ (in mM: 5 $BaCl_2$, 1 $MgCl_2$, 10 HEPES, 40 tetraethylammonium chloride, 10 glucose, 87.5 CsCl pH 7.2). Current data shown were elicited by a train of 100 ms test pulses at 0.066 Hz from −100 mV and/or −80 mV to various potentials (min. −20 mV, max. +30 mV). Drugs were perfused directly into the vicinity of the cells using a microperfusion system.

Normalized dose-response curves were fit (Sigmaplot 4.0, SPSS Inc., Chicago, Ill.) by the Hill equation to determine $IC_{50}$ values. Steady-state inactivation curves were plotted as the normalized test pulse amplitude following 5 s inactivating prepulses at +10 mV increments. Inactivation curves were fit (Sigmaplot 4.0) with the Boltzman equation, $I_{peak}$ (normalized)=$1/(1+\exp((V-V_h)z/25.6))$, where V and $V_h$ are the conditioning and half inactivation potentials, respectively, and z is the slope factor.

EXAMPLE 2

Synthesis of Illustrative Compound of Formula (1)

A. Synthesis of $MeSO_2(CH_2)_6Cl$.

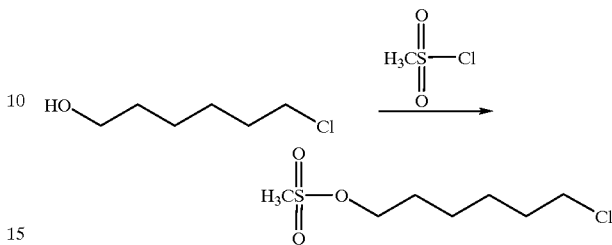

1-Chloro-6-hexanol (2 ml, 15 mM) was dissolved in dry THF (40 ml) and the flask purged with nitrogen. To this solution was added DIEA (3.2 ml, 18 mM) followed by the slow addition of methane sulfonyl chloride. The solution was stirred for 5.5 hours. The reaction mixture was extracted with EtOAc and washed with water and 10% HCl. The solution was concentrated under reduced pressure and used without further purification; yield 3.8 g.

B. Synthesis of Formula 1(a).

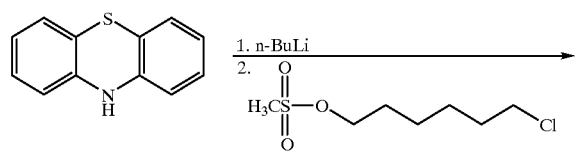

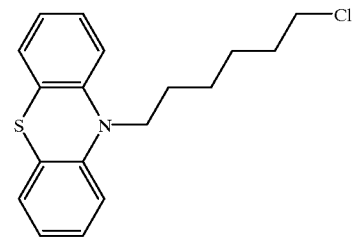

Phenanthrothiazine (2.0 g, 10 mM) was dissolved in ~70 ml dry THF the flask flushed with nitrogen and cooled to −78° C. To the cooled solution was added n-butyl lithium (4.8 ml, 12 mM) and allowed to stir for 1 hour at −78° C. followed by warming to room temperature. The product from the above reaction was added and allowed to stir overnight. The reaction was quenched with ~30 ml water. The THF layer was separated and the aqueous layer extracted with ether. The combined organic layers were then washed with water. The product was purified by silica gel chromatography.

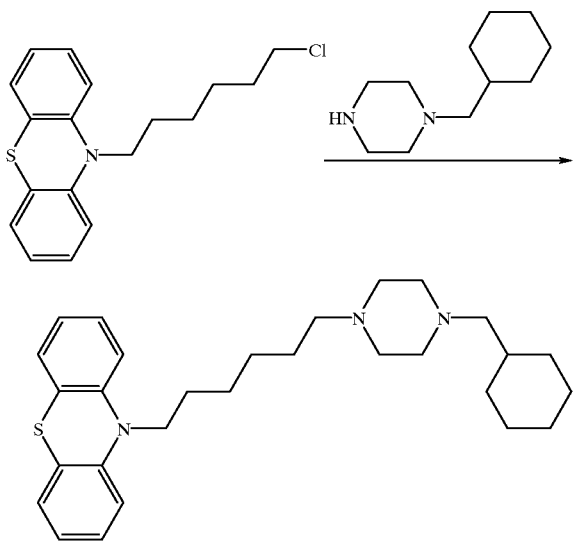

The phenanthrothiazine derivative (0.3 g, 0.95 mM) and the piperazine shown above (0.321 g, 1.76 mM) was dissolved in 5 ml dry THF along with NaI (cat) and $K_2CO_3$ (~0.5 g) and heated to 40° C. overnight. The reaction mixture was diluted with EtOAc and washed with water (4×) and brine (1×) and the solvent removed under reduced pressure. The residue was purified by column (silica gel hexane/EtOAc) to give the desired product. Some of the compounds in this series required HPLC purification. The compounds were kept out of direct light during the purification and after isolation.

EXAMPLE 3

Channel Blocking Activities of Various Invention Compounds

Using the procedure set forth in Example 1, various compounds of the invention were tested for their ability to block N-type calcium channels. The results are shown in Tables 1–2, where $IC_{50}$ is given in μM (micromolar). Table 1 represents results for compounds of formula (1a) where Z is N and Y is S; and Table 2 represents the results the results for compounds of formula (1b) where Z is N and Y is S. In all cases, $1^1$, $1^2$ and $1^3$ are 0.

TABLE 1

Formula (1a), Z is N, Y is S

| $X^1$ | n | $X^2$ | Ar | $IC_{50}$ | % reversibility |
|---|---|---|---|---|---|
| $(CH_2)_6$ | 1 | —$CH_3$ | | ±2 | 63 |
| $(CH_2)_6$ | 1 | —$CH_2$—CH=CH— | φ | 2–3 | 20 |
| $(CH_2)_6$ | 1 | $CH_2$ | φ | ±2 | 43 |
| $(CH_2)_3$ | 1 | —$CH_2CH$=CH— | φ | 5 | 20 |

TABLE 2

Formula (1b), Z is N, Y is S

| $X^1$ | n | $X^2$ | Cy | $IC_{50}$ | % reversibility |
|---|---|---|---|---|---|
| $(CH_2)_3$ | 1 | $CH_2$ | cyclohexyl | 3.2 | 7 |
| $(CH_2)_6$ | 1 | $CH_2$ | cyclohexyl | 3.2 | 9 |

What is claimed is:

1. A method to treat conditions associated with undesired calcium channel activity in a subject which method comprises administering to a subject in need of such treatment a compound of the formula

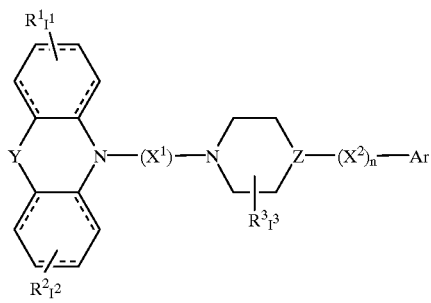

(1a)

or

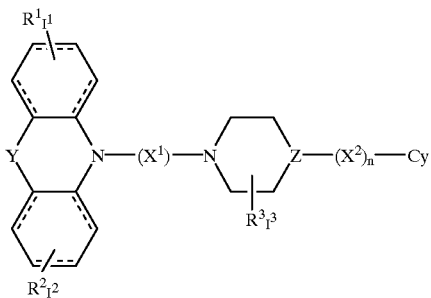

(1b)

or the salts thereof,
wherein Z is N or CH;
wherein n is 0 or 1;
$X^1$ and $X^2$ are linkers;
Ar represents one or two substituted or unsubstituted aromatic or heteroaromatic rings, and
Cy represents one or two substituted or unsubstituted aliphatic cyclic or heterocyclic moieties, or consists of one substituted or unsubstituted aliphatic cyclic or heterocyclic moiety and one substituted or unsubstituted aromatic or heteroaromatic moiety,
Y is O, S, NR or $CR_2$ where R is H or alkyl (1–6C);
each $l^1$ and $l^2$ is independently 0–4;
$l^3$ is 0 or 1;
each of $R^1$, $R^2$ and $R^3$ is independently alkyl (1–6C), aryl (6–10C) or arylalkyl (7–16C) optionally containing 1–4 heteroatoms selected from the group consisting of halo, N, P, O, and S or may independently be halo, OR, SR, $NR_2$, OOCR, NROCR, COR, COOR, $CONR_2$, $CF_3$, CN or $NO_2$, wherein R is H or alkyl (1–6C), and wherein the dotted lines represent optional π-bonds, or compounds of formulas (1a) or (1b) where $(X^2)_n$Ar or $(X^2)_n$Cy is replaced by alkyl (1–6C).

2. The method of claim 1 wherein at least one of $R^1$, $R^2$ and $R^3$ is a halo substituent.

3. The method of claim 1 wherein the compound of formula (1) is of the formula (1a)

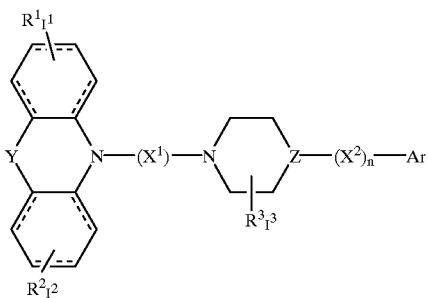

wherein Y, Z, $R^1$, $R^2$, $R^3$, $l^1$, $l^2$, $l^3$, $X^1$, $X^2$ n, and Ar are defined as in claim 1, or wherein $—(X^2)_n—Ar$ is replaced by alkyl (1–6C).

4. The method of claim 3 wherein Ar represents one or two unsubstituted phenyl moieties.

5. The method of claim 3 wherein n is 1 and $X^2$ represents a linker which spaces Ar from Z at a distance of 3–20 Å.

6. The method of claim 5 wherein n is 1 and $X^2$ contains at least one heteroatom selected from N and O.

7. The method of claim 5 wherein n is 1, Ar represents one unsubstituted phenyl moiety and $X^2$ represents $—(CH_2)_{1-10}—$ or $—CO(CH_2)_{1-9}—$ or $—(CH_2)_{1-5}—CH=CH—(CH_2)_{0-3}—$ or $—NH(CH_2)_{1-8}—$.

8. The method of claim 5 wherein Ar represents two phenyl moieties and $X^2$ is of the formula $—(CH_2)_{0-10}—CH$ or $—CO(CH_2)_{0-9}CH$.

9. The method of claim 3 wherein $—(X^2)_n Ar$ is replaced by methyl or ethyl.

10. The method of claim 3 wherein $l^3$ is 0.

11. The method of claim 3 wherein $l^1$ and $l^2$ are 0.

12. The method of claim 1 wherein the compound of formula (1) is of the formula (1b)

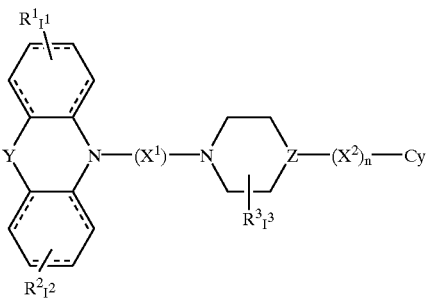

wherein Y, Z, $R^1$, $R^2$, $R^3$, $X^1$, $X^2$, $l^1$, $l^2$ and Cy are as defined in claim 1.

13. The method of claim 12 wherein Cy represents one or two cyclohexyl moieties or a cyclohexyl moiety and a phenyl moiety.

14. The method of claim 12 wherein n is 1 and $X^2$ represents a linker which spaces Cy from Z at a distance of 3–20 Å.

15. The method of claim 12 wherein n is 1 and $X^2$ contains at least one heteroatom selected from N and O.

16. The method of claim 13 wherein Cy is one cyclohexyl moiety, n is 1 and $X^2$ represents $—(CH_2)_{1-10}—$ or $—CO(CH_2)_{1-9}—$ or $—(CH_2)_{1-5}—CH=CH—(CH_2)_{0-3}—$ or $—NH(CH_2)_{1-8}—$.

17. The method of claim 12 wherein Cy represents two cyclohexyl moieties or a cyclohexyl moiety and a phenyl moiety.

18. The method of claim 17 wherein $X^2$ is $—(CH_2)_{0-9}—CH—$ or $CO(CH_2)_{1-8}$ $CH—$.

19. The method of claim 12 wherein $l^3$ is 0.

20. The method of claim 12 wherein $l^1$ and $l^2$ are 0.

21. The method of claim 1 wherein $X^1$ represents a linker which spaces the benzhydril moiety from N at a distance of 3–20 Å.

22. The method of claim 21 wherein $X^1$ contains at least one heteroatom selected from O and N.

23. The method of claim 20 wherein $X^1$ represents $—(CH_2)_{1-10}—$, $—(CH_2)_{1-5}—CH=CH—(CH_2)_{0-3}—$ or $—(CH_2)_{1-9}CO—$.

24. A pharmaceutical composition for use in treating conditions characterized by undesired calcium channel activity which composition comprises, in admixture with a pharmaceutically acceptable excipient, a dosage amount of at least one compound of the formula

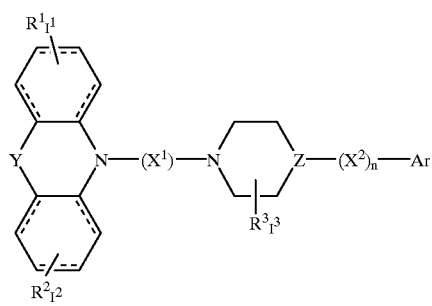

or

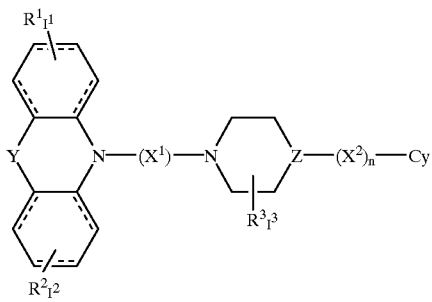

or salts thereof, wherein Z is N or CH;

wherein n is 0 or 1;

$X^1$ and $X^2$ are linkers;

Ar represents one or two substituted or unsubstituted aromatic or heteroaromatic rings, and Cy represents one or two substituted or unsubstituted aliphatic cyclic or heterocyclic moieties, or consists of one substituted or unsubstituted aliphatic cyclic or heterocyclic moiety and one substituted or unsubstituted aromatic or heteroaromatic moiety, Y is O, S, NR or CR$_2$ where R is H or alkyl (1–6C);

each l$^1$ and l$^2$ is independently 0–4;

l$^3$ is 0 or 1;

each of R$^1$, R$^2$ and R$^3$ is independently alkyl (1–6C), aryl (6–10C) or arylalkyl (7–16C) optionally containing 1–4 heteroatoms selected from the group consisting of halo, N, P, O, and S or may independently be halo, OR, SR, NR$_2$, OOCR, NROCR, COR, COOR, CONR$_2$, CF$_3$, CN or NO$_2$, wherein R is H or alkyl (1–6C), and wherein the dotted lines represent optional π-bonds, or compounds of formulas (1a) or (1b) where (X$^2$)$_n$Ar or (X$^2$)$_n$Cy is replaced by alkyl (1–6C).

25. A library comprising at least ten different compounds of the formula

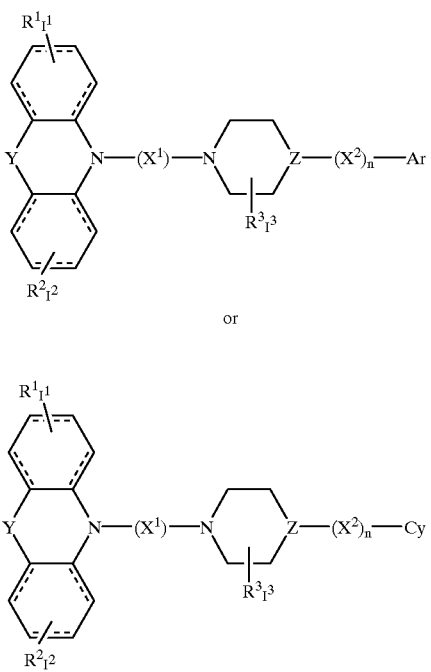

or salts thereof, wherein Z is N or CH;

wherein n is 0 or 1;

X$^1$ and X$^2$ are linkers;

Ar represents one or two substituted or unsubstituted aromatic or heteroaromatic rings, and Cy represents one or two substituted or unsubstituted aliphatic cyclic or heterocyclic moieties, or consists of one substituted or unsubstituted aliphatic cyclic or heterocyclic moiety and one substituted or unsubstituted aromatic or heteroaromatic moiety, Y is O, S, NR or CR$_2$ where R is H or alkyl (1–6C);

each l$^1$ and l$^2$ is independently 0–4;

l$^3$ is 0 or 1;

each of R$^1$, R$^2$ and R$^3$ is independently alkyl (1–6C), aryl (6–10C) or arylalkyl (7–16C) optionally containing 1–4 heteroatoms selected from the group consisting of halo, N, P, O, and S or may independently be halo, OR, SR, NR$_2$, OOCR, NROCR, COR, COOR, CONR$_2$, CF$_3$, CN or NO$_2$, wherein R is H or alkyl (1–6C), and wherein the dotted lines represent optional π-bonds, or compounds of formulas (1a) or (1b) where (X$^2$)$_n$Ar or (X$^2$)$_n$Cy is replaced by alkyl (1–6C).

26. A method to identify a compound which antagonizes a target channel which method comprises contacting host cells displaying said target channel in the presence of an agonist for said channel and with the members of the library of claim 25;

assessing the ability of the members of the library to affect the response of the channel to its agonist; and identifying as an antagonist any member of the library which diminishes the response of the channel to its agonist.

27. The method of claim 26 wherein the channel is an ion channel.

* * * * *